(12) United States Patent
Van Der Laan et al.

(10) Patent No.: US 8,790,894 B2
(45) Date of Patent: Jul. 29, 2014

(54) MUTANT CELLOBIOHYDROLASE

(75) Inventors: Jan Metske Van Der Laan, Breda (NL); Margot Elisabeth Francoise Schooneveld-Bergmans, Delft (NL); Denise Ilse Jacobs, Pijnacker (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/982,419

(22) PCT Filed: Jan. 30, 2012

(86) PCT No.: PCT/EP2012/051416
§ 371 (c)(1),
(2), (4) Date: Jul. 29, 2013

(87) PCT Pub. No.: WO2012/104239
PCT Pub. Date: Aug. 9, 2012

(65) Prior Publication Data
US 2013/0309729 A1 Nov. 21, 2013

Related U.S. Application Data

(60) Provisional application No. 61/437,804, filed on Jan. 31, 2011.

(30) Foreign Application Priority Data

Jan. 31, 2011 (EP) .................................... 11152691

(51) Int. Cl.
*C12N 9/42* (2006.01)
*C12P 1/00* (2006.01)

(52) U.S. Cl.
USPC ..... 435/41; 435/209; 435/252.3; 435/254.11; 435/183; 435/320.1; 536/23.2

(58) Field of Classification Search
None
See application file for complete search history.

(56) References Cited

U.S. PATENT DOCUMENTS

2013/0145501 A1  6/2013  Sagt et al.

FOREIGN PATENT DOCUMENTS

WO  2010122141 A1  10/2010

OTHER PUBLICATIONS

International Search Report for PCT/EP2012/051416 Mailed April 5, 2012.
Grassick et al., "Three-Dimensional Structure of a Thermostable Native Cellobiohydrolkase, CHB IB, and Molecular Characterization of CEL7 Gene From the Filamentous Fungus, *Talaromyces emersonii*," Eur. J. Biochem, vol. 271, No. 22, pp. 4495-4506, (2004).
Tuohy et al., "Kinetic Parameters and Mode of Action of the Cellobiohydrolases Produced by *Talaromyces emersonii*," Biochimica Et Biophysica Acta, vol. 1596, No. 2, pp. 366-380, (2002).
Moloney et al., "Isolation of Mutants of *Talaromyces emersonii* CBS 814.70 With Enhanced Cellulase Activity," Enzyme and Microbial Technology, vol. 5, No. 4, pp. 260-264, (1983).

*Primary Examiner* — Nashaat Nashed
(74) *Attorney, Agent, or Firm* — Miles & Stockbridge, P.C.

(57) ABSTRACT

The invention relates to Mutant cellobiohydrolase, being a mutant of SEQ ID NO:1, having a substitution at position N247(I,F,H,W) of SEQ ID NO: 1, wherein the mutant cellobiohydrolase has at least 50% sequence identity with SEQ ID NO: 1, and wherein the mutant cellobiohydrolase has CBHI activity.

22 Claims, No Drawings

MUTANT CELLOBIOHYDROLASE

CROSS REFERENCE TO RELATED APPLICATIONS

This application is a §371 National Stage Application of PCT/EP2012/051416, filed Jan. 30, 2012, which claims priority to European Application No. 11152691.9, filed Jan. 31, 2011, and U.S. Provisional Application No. 61/437,804, filed Jan. 31, 2011.

BACKGROUND OF THE INVENTION

1. Field of the Invention

The invention is directed to novel mutant cellobiohydrolases and cellobiohydrolase comprising compositions which have improved CBHI activity. Specifically, the present invention relates to a family of cellobiohydrolases from fungi and bacteria which are related to CBH-I produced by *Talaromyces emersonii*, which have certain mutations.

2. Description of Related Art

Cellulases are enzymes which are capable of hydrolysis of the beta-D-glucosidic linkages in celluloses. Cellulolytic enzymes have been traditionally divided into three major classes: endoglucanases, exoglucanases or cellobiohydrolases and beta.-glucosidases (Knowles, J. et al., (1987), TIBTECH 5, 255-261); and are known to be produced by a large number of bacteria, yeasts and fungi.

Primary among the applications that have been developed for the use of cellulolytic enzymes are those involving degrading (wood) cellulose pulp into sugars for (bio)ethanol production, textile treatments like 'stone washing' and 'biopolishing', and in detergent compositions.

Thus, cellulases have been shown to be effective in many industrial processes. Accordingly, there has been a trend in the field to search for specific cellulase compositions or components which have particularly effective performance profiles with respect to one or more specific applications. In this light, cellulases produced (expressed) in fungi and bacteria have been subject of attention. For example, cellulase produced by certain fungi such as *Trichoderma* spp. (especially *Trichoderma longibrachiatum*) have been given much attention because a complete cellulase system capable of degrading crystalline forms of cellulose is readily produced in large quantities via fermentation procedures. This specific cellulase complex has been extensively analyzed to determine the nature of its specific components and the ability of those components to perform in industrial processes. For example, Wood et al., "Methods in Enzymology", 160, 25, pages 234 et seq. (1988), disclose that complete fungal cellulase systems comprise several different enzyme classifications including those identified as exo-cellobiohydrolases (EC 3.2.1.91) ("CBH"), endoglucanases (EC 3.2.1.4) ("EG"), and beta-glucosidases (EC 3.2.1.21) ("BG"). The fungal cellulase classifications of CBH, EG and BG can be further expanded to include multiple components within each classification. Some genetic modification of CBH-I has been proposed. S. P. Voutilainen, P. G. Murray, M. G. Tuohy and A. Koivula, Protein Engineering, Design and Selection, pp. 1-11, 2009, discloses the expression of *Talaromyces emersonii* cellobiohydrolase CEL7A in *Saccharomyces cerevisiae* and rational mutagenisis to improve its thermostability and activity. In this disclosure the mutant N54C/P191C showed increased thermostability and improved activity $k_{cat}$ 35.9 min-1 (table II). However this activity is still relatively low.

WO2010/122141 discloses a CBH-I from *Talararomyces emersonii* and polynucleotides encoding the CBH-I, and cells that incorporate these polynucleotides. The amino acid sequence of the CBH-I of WO2010/122141 is herein given as SEQ ID NO: 1.

Despite knowledge in the art related to many cellulase compositions having applications in some or all of the above areas, there is a continued need for new cellulase compositions which have improved activity under conditions of lignocellulose conversion. Therefore there is a need to improve the existing CBH-I activity, alone or in combination with other cellulases.

SUMMARY

An object of the invention is to provide novel variant CBH-I or CBH-I-like cellulase compositions which have improved CBHI activity.

CBHI activity is measured as described in the examples. It is a further object of the invention to provide for novel variant CBH-I or CBH-I-like cellulase compositions which have improved performance under conditions of thermal stress.

It is a further object of the invention to provide for novel variant CBH-I or CBH-I-like cellulase containing compositions which will provide excellent performance in degradation of biological material, such as lignocellulose.

It is a further object of the invention to provide for novel variant CBH-I or CBH-I-like cellulase composition which have improved characteristics for the reduction of biomass, as an additive in animal feed, in starch processing and in baking applications.

One or more of these objects are attained according to the invention. According to the present invention, there is provided a mutant cellobiohydrolase, being a mutant of SEQ ID NO:1, having a substitution at position N247(I,F,H,W) of SEQ ID NO: 1, wherein the mutant cellobiohydrolase has at least 50% sequence identity with SEQ ID NO: 1, and wherein the mutant cellobiohydrolase has CBHI activity.

In an embodiment, the mutant has substitution N247F. In another embodiment, the mutant has substitution N247H.

BRIEF DESCRIPTION OF THE SEQUENCE LISTING

SEQ ID NO: 1 SEQ ID NO: 1 sets out the aminoacid sequence of CBH-I from *Talaromyces emersonii*, designated as SEQ ID NO: 1 in WO2010/122141.

SEQ ID NO: 2 SEQ ID NO: 2 sets out the signal sequence for the cellobiohydrolase of SEQ ID NO: 1.

SEQ ID NO: 3 SEQ ID NO: 3 sets out the DNA sequence of CBH-I (EBA205).

DETAILED DESCRIPTION OF A PREFERRED EMBODIMENT

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element.

The mutant cellobiohydrolase according to the invention, being a mutant of SEQ ID NO: 1, has a substitution at position N247(I,F,H,W) of SEQ ID NO: 1, wherein the mutant cellobiohydrolase has at least 50% sequence identity with SEQ ID NO: 1, and wherein the mutant cellobiohydrolase has CBHI activity.

In an embodiment, the mutant has substitution N247F. In another embodiment, the mutant has substitution N247H.

In a further embodiment, the CBH-I has, alone or in combination with the previously mentioned mutations, a substitution or deletion at a position corresponding to one or more of residues F445, K163, G357, S36, D77, and/or Q232. The mutations at these positions may be a substitution of C, P, G, A, V, L, I, M, F, W, Y, H, S, T, N, Q, D, E, K, R or a deletion. In a further embodiment thereof, the mutant has one or more of the following substitutions: F445I, K163N, G357R, S36E, D77M and/or Q232A.

In another embodiment, the cellobiohydrolase mutant has, alone or in combination with the previously mentioned mutations, a substitution or deletion at a position corresponding to one or more of residues T52, V101, S192, T198, T344, D346, A375 or A376 of SEQ ID NO:1. The mutations at these positions may be a substitution of C, P, G, A, V, L, I, M, F, W, Y, H, S, T, N, Q, D, E, K, R or a deletion. In a further embodiment thereof, the mutant has one or more of the following substitutions: T52(G,M,Y,D,H,K,R), V101(T,I,F,H), S192(A,I,F,Q,H), T198(A,C,V,P,D,H), T246(G,A,Y,N,H), N247(I,F,W), T344(A,S,C,L,I,Y,W), D346(P,F,G,R), A375 (G,I,W,Y,H,K,R) and/or A376(T,V,L,Y,W,D). In an embodiment thereof, the mutant has one or more of the substitutions: T52(M,D,R), V101(I,F), S192F, T198A, N247F, T344(C,L), A375(Y,H), preferably A375H and/or A376D.

In another embodiment, the cellobiohydrolase mutant has, alone or in combination with the previously mentioned mutations, a substitution or deletion at a position corresponding to one or more of residues A6, T7, L34, V41, Y47, T48, S99, V144, S171, L177, N194, N195, A196, I200, S205, T243, Y244, S245, Y249, P255, Q337, D343, H350, V367, D372, T393, and/or V396.

Herein, a cellobiohydrolase (EC 3.2.1.91) is any polypeptide which is capable of catalysing the hydrolysis of 1,4-β-D-glucosidic linkages in cellulose or cellotetraose, releasing cellobiose from the non-reducing ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase. "Cellobiohydrolase" is herein abbreviated as "CBH". Cellobiohydrolase-I is herein abbreviated as "CBH-I". "Mutant Cellobiohydrolase", is abbreviated as "Mutant CBH" or mutant. "Mutant CBH polynucleotide", is herein a polynucleotide that encodes the Mutant CBH.

In the Mutant CBH has at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with SEQ ID NO: 1.

Herein mutations are indicated by one letter aminoacids and positions of these amino acids. For example, A6 herein indicates an amino acid (one letter code) at a certain position in SEQ ID NO:1, here A (Alanine) at position 6 of the protein. A6 (L/N/Q/G/V/I/Y/S/E/K) indicates herein mutation of amino acid at a certain position, here A (Alanine) at position 6 of the protein is exchanged for any of L (Leucine), N (Asparagine), Q (Glutamine), G (Glycine), V (Valine), I (Isoleucine), Y (Tyrosine), S (Serine), E (Glutamic acid) or K (Lysine).

A Mutant CBH of the invention may have one or more alternative and/or additional activities other than that of cellobiohydrolase activity, for example one of the other cellulase activities mentioned hereinafter.

A Mutant CBH according to the invention may modify a carbohydrate material by chemically modifying or physically modifying such material. Chemical modification of the carbohydrate material may result in the degradation of such material, for example by hydrolysis, oxidation or other chemical modification such as by the action of a lyase. Physical modification may or may not be accompanied by chemical modification.

The mutant may have one or more of the following enzyme activities or an enzyme composition comprising the mutant CBH enzyme according to the invention may comprise one or more of the following enzymes:

Endo-1,4-β-glucanases (EG) and exo-cellobiohydrolases (CBH, e.g. CBH-I or CBH-II) catalyze the hydrolysis of insoluble cellulose to cellooligosaccharides (cellobiose as a main product), while β-glucosidases (BG) convert the oligosaccharides, mainly cellobiose and cellotriose to glucose. EG, CBH, BG, xylanase and pectinase enzyme activities may be activities of the Mutant CBH or activities present in other constituents of the peptide composition that comprise Mutant CBH.

Xylanases together with other accessory enzymes, for example α-L-arabinofuranosidases, feruloyl and acetylxylan esterases, glucuronidases, and β-xylosidases) catalyze the hydrolysis of hemicelluloses.

Pectinases, for example an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase, an α-arabinofuranosidase.

As set out above, a Mutant CBH of the invention will typically have cellobiohydrolase activity. However, a Mutant CBH of the invention may have one or more of the activities set out above in addition to or alternative to that activity. Also, a Mutant CBH composition of the invention as described herein may have one or more of the activities mentioned above in addition to that provided by the cellobiohydrolase mutant of the invention having cellobiohydrolase activity or these activities may be present in an enzyme composition comprising the mutant CBH enzyme of the invention.

Polynucleotide Sequence

With the Mutant CBH and its aminoacid sequence as disclosed herein, the skilled person may determine suitable polynucleotides that encode the Mutant CBH.

The invention therefore provides polynucleotide sequences comprising the gene encoding the Mutant CBH, as well as its coding sequence.

The polynucleotides of the invention may be isolated or synthesized. Synthetic polynucleotides may be prepared using commercially available automated polynucleotide synthesizers.

The Mutant CBH polypeptides and Mutant CBH polynucleotides herein may be synthetic polypeptides, respectively polynucleotides. The synthetic polynucleotides may be optimized in codon use, preferably according to the methods described in WO2006/077258 and/or PCT/EP2007/055943, which are herein incorporated by reference. PCT/EP2007/055943 addresses codon-pair optimization.

The term refers to a polynucleotide molecule, which is a ribonucleic acid (RNA) or deoxyribonucleic acid (DNA)

molecule, either single stranded or double stranded. A polynucleotide may either be present in isolated form, or be comprised in recombinant nucleic acid molecules or vectors, or be comprised in a host cell.

The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art.

By "isolated" polypeptide or protein is intended a polypeptide or protein removed from its native environment. For example, recombinantly produced polypeptides and proteins expressed in host cells are considered isolated for the purpose of the invention as are native or recombinant polypeptides which have been substantially purified by any suitable technique such as, for example, the single-step purification method disclosed in Smith and Johnson, Gene 67:31-40 (1988).

The polynucleotides of the present invention, such as a polynucleotide encoding the Mutant CBH can be isolated or synthesized using standard molecular biology techniques and the sequence information provided herein.

The polynucleotide encoding the Mutant CBH of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Transformation

The polynucleotides according to the invention may be expressed in a suitable host. Therefore standard transformation techniques may be used.

The invention further relates to a nucleic acid construct comprising the polynucleotide as described before, e.g. a vector.

Another aspect of the invention thus pertains to vectors, including cloning and expression vectors, comprising a polynucleotide of the invention encoding a CBH protein or a functional equivalent thereof and methods of growing, transforming or transfecting such vectors in a suitable host cell, for example under conditions in which expression of a CBH-I of the invention occurs. As used herein, the term "vector" refers to a nucleic acid molecule capable of transporting another nucleic acid to which it has been linked.

Polynucleotides of the invention can be incorporated into a recombinant replicable vector, for example a cloning or expression vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below.

It will be appreciated by those skilled in the art that the design of the expression vector can depend on such factors as the choice of the host cell to be transformed, the level of expression of protein desired, etc. The vectors, such as expression vectors, of the invention can be introduced into host cells to thereby produce proteins or peptides, encoded by nucleic acids as described herein (e.g. CBH proteins, mutant forms of CBH proteins, fragments, variants or functional equivalents thereof. The vectors, such as recombinant expression vectors, of the invention can be designed for expression of CBH proteins in prokaryotic or eukaryotic cells.

For example, CBH proteins can be expressed in bacterial cells such as $E.\ coli$, insect cells (using baculovirus expression vectors), filamentous fungi, yeast cells or mammalian cells. Suitable host cells are discussed further in Goeddel, *Gene Expression Technology: Methods in Enzymology* 185, Academic Press, San Diego, Calif. (1990). Representative examples of appropriate hosts are described hereafter.

Appropriate culture mediums and conditions for the above-described host cells are known in the art.

For most filamentous fungi and yeast, the vector or expression construct is preferably integrated in the genome of the host cell in order to obtain stable transformants. However, for certain yeasts also suitable episomal vectors are available into which the expression construct can be incorporated for stable and high level expression, examples thereof include vectors derived from the 2µ and pKD1 plasmids of *Saccharomyces* and *Kluyveromyces*, respectively, or vectors containing an AMA sequence (e.g. AMA1 from *Aspergillus*). In case the expression constructs are integrated in the host cells genome, the constructs are either integrated at random loci in the genome, or at predetermined target loci using homologous recombination, in which case the target loci preferably comprise a highly expressed gene.

Accordingly, expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

When the polypeptide according to the invention is to be secreted from the host cell into the cultivation medium, an appropriate signal sequence can be added to the polypeptide in order to direct the de novo synthesized polypeptide to the secretion route of the host cell. The person skilled in the art knows to select an appropriate signal sequence for a specific host.

The vector may further include sequences flanking the polynucleotide giving rise to RNA which comprise sequences homologous to eukaryotic genomic sequences or viral genomic sequences. This will allow the introduction of the polynucleotides of the invention into the genome of a host cell.

An integrative cloning vector may integrate at random or at a predetermined target locus in the chromosome(s) of the host cell into which it is to be integrated.

The vector system may be a single vector, such as a single plasmid, or two or more vectors, such as two or more plasmids, which together contain the total DNA to be introduced into the genome of the host cell.

The vector may contain a polynucleotide of the invention oriented in an antisense direction to provide for the production of antisense RNA.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-percipitation, DEAE-dextran-mediated transfection, transduction, infection, lipofection, cationic lipidmediated transfection or electroporation. Suitable methods for transforming or transfecting host cells can be found in Sambrook, et al. (*Molecular Cloning: A Laboratory Manual, 2nd, ed. Cold Spring Harbor Laboratory*, Cold Spring Harbor Laboratory Press, Cold Spring Harbor, N.Y., 1989), Davis et al., *Basic Methods in Molecular Biology* (1986) and other laboratory manuals.

As indicated before, the invention provides an isolated polypeptide having the amino acid sequence according to SEQ ID NO: 1, or SEQ ID NO: 2 with the mutations indicated in claim 1.

The Mutant CBH according to the invention can be recovered and purified from recombinant cell cultures by methods known in the art. Most preferably liquid chromatography such as high performance liquid chromatography ("HPLC"), is employed for purification which may comprise, but is not limited to the use of ion-exchange chromatography, hydrophobic interaction chromatography, affinity chromatography and size exclusion chromatography to further separate the target CBH from the bulk protein to enable recovery of the target CBH in a highly purified state.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue or a pyroglutamate, in some cases as a result of host-mediated processes. Pyroglutamic acid (also known as 5-oxoproline, pidolic acid, or pyroglutamate for its basic form) is an uncommon amino acid derivative in which the free amino group of glutamic acid cyclizes to form a lactam. It is found in many proteins including bacteriorhodopsin.

The invention also features biologically active fragments of the polypeptides according to the invention.

Provided also are host cells, comprising a polynucleotide or vector of the invention. The polynucleotide may be heterologous to the genome of the host cell. The term "heterologous", usually with respect to the host cell, means that the polynucleotide does not naturally occur in the genome of the host cell or that the polypeptide is not naturally produced by that cell.

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are cells from filamentous fungi, such as *Aspergillus niger*.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

If desired, a cell as described above may be used to in the preparation of a polypeptide according to the invention. Such a method typically comprises cultivating a host cell (e.g. transformed or transfected with an expression vector as described above) under conditions to provide for expression (by the vector) of a coding sequence encoding the polypeptide, and optionally recovering the expressed polypeptide. Polynucleotides of the invention can be incorporated into a recombinant replicable vector, e.g. an expression vector. The vector may be used to replicate the nucleic acid in a compatible host cell. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell.

Preferably the polypeptide is produced as a secreted protein in which case the nucleotide sequence encoding a mature form of the polypeptide in the expression construct is operably linked to a nucleotide sequence encoding a signal sequence. Preferably the signal sequence is native (homologous) to the nucleotide sequence encoding the polypeptide. Alternatively the signal sequence is foreign (heterologous) to the nucleotide sequence encoding the polypeptide, in which case the signal sequence is preferably endogenous to the host cell in which the nucleotide sequence according to the invention is expressed. Examples of suitable signal sequences for yeast host cells are the signal sequences derived from yeast a-factor genes. Similarly, a suitable signal sequence for filamentous fungal host cells is e.g. a signal sequence derived from a filamentous fungal amyloglucosidase (AG) gene, e.g. the *A. niger* glaA gene. This may be used in combination with the amyloglucosidase (also called (gluco) amylase) promoter itself, as well as in combination with other promoters. Hybrid signal sequences may also be used with the context of the present invention.

Preferred heterologous secretion leader sequences are those originating from the fungal amyloglucosidase (AG) gene (glaA-both 18 and 24 amino acid versions e.g. from *Aspergillus*), the α-factor gene (yeasts e.g. *Saccharomyces* and *Kluyveromyces*) or the α-amylase gene (*Bacillus*).

The vectors may be transformed or transfected into a suitable host cell as described above to provide for expression of a polypeptide of the invention. This process may comprise culturing a host cell transformed with an expression vector as described above under conditions to provide for expression by the vector of a coding sequence encoding the polypeptide.

Herein standard isolation, hybridization, transformation and cloning techniques are used (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Homology & Identity

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of squence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, *EMBOSS: The European Molecular Biology Open Software Suite* (2000) Rice, P. Longden, I. and Bleasby, A. Trends in Genetics 16, (6) pp 276-277, http://emboss.bioinformatics.nl/). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity". Preferably the longest identity is used for calculating the identity.

Host Cells

The invention thus provides host cells transformed or transfected with or comprising a polynucleotide or vector of the invention. Preferably the polynucleotide is carried in a vector for the replication and expression of the polynucleotide. The cells will be chosen to be compatible with the said vector and may for example be prokaryotic (for example bacterial), fungal, yeast or plant cells.

A heterologous host may also be chosen wherein the polypeptide of the invention is produced in a form which is substantially free from other cellulose-degrading or hemicellulose degrading enzymes. This may be achieved by choosing a host which does not normally produce such enzymes.

The invention encompasses processes for the production of the polypeptide of the invention by means of recombinant expression of a DNA sequence encoding the polypeptide. For this purpose the DNA sequence of the invention can be used for gene amplification and/or exchange of expression signals, such as promoters, secretion signal sequences, in order to allow economic production of the polypeptide in a suitable homologous or heterologous host cell. A homologous host cell is a host cell which is of the same species or which is a variant within the same species as the species from which the DNA sequence is derived.

Suitable host cells are preferably prokaryotic microorganisms such as bacteria, or more preferably eukaryotic organisms, for example fungi, such as yeasts or filamentous fungi, or plant cells. In general, yeast cells are preferred over fungal cells because they are easier to manipulate. However, some proteins are either poorly secreted from yeasts, or in some cases are not processed properly (e.g. hyperglycosylation in yeast). In these instances, a fungal host organism should be selected.

The host cell may over-express the polypeptide, and techniques for engineering over-expression are well known. The host may thus have two or more copies of the encoding polynucleotide (and the vector may thus have two or more copies accordingly).

Bacteria from the genus *Bacillus* are very suitable as heterologous hosts because of their capability to secrete proteins into the culture medium. Other bacteria suitable as hosts are those from the genera *Streptomyces* and *Pseudomonas*. A preferred yeast host cell for the expression of the DNA sequence encoding the polypeptide is of the genera *Saccharomyces, Kluyveromyces, Hansenula, Pichia, Yarrowia*, and *Schizosaccharomyces*.

More preferably a yeast host cell is selected from the group consisting of the species *Saccharomyces cerevisiae, Kluyveromyces lactis* (also known as *Kluyveromyces marxianus* var. *lactis*), *Hansenulapolymorpha, Pichia pastoris, Yarrowia lipolytica* and *Schizosaccharomyces pombe*.

Most preferred are, however, (e.g. filamentous) fungal host cells. Preferred filamentous fungal host cells are selected from the group consisting of the genera *Aspergillus, Trichoderma/Hypocrea, Fusarium, Disporotrichum, Penicillium, Acremonium, Neurospora, Thermoascus, Myceliophtora, Sporotrichum, Thielavia, Chryosporium, Fusarium, Humicola, Neurospora* and *Talaromyces*.

More preferably a filamentous fungal host cell is of the species *Aspergillus oryzae, Aspergillus sojae, Aspergillus nidulans*, or a species from the *Aspergillus niger* Group. These include, but are not limited to *Aspergillus niger, Aspergillusawamori, Aspergillus tubingensis, Aspergillus aculeatus, Aspergillus foetidus, Aspergillus nidulans, Aspergillus japonicus, Aspergillus oryzae* and *Aspergillus ficuum* and further consisting of the species

*Trichoderma reeseil Hypocrea jacorina, Fusarium graminearum, Talaromyces emersonii, Penicillium decumbens, Acremonium alabamense, Neurospora crassa, Myceliophtora thernaophilurri, Sporotrichum cellulophilum, Disporotrichum dimorphosphorum, Talaromyces emersonii, Talaromyces stipitatus* and *Thielavia terrestris*.

Examples of preferred expression hosts within the scope of the present invention are fungi such as *Aspergillus* species, *Penicillium species* and *Trichoderma* species; bacteria such as *Bacillus* species, e.g. *Bacillus subtilis, Bacillus licheniformis, Bacillus amyloliquefaciens, Pseudomonas* species; and yeasts such as *Kluyveromyces* species, e.g. *Kluyveromyces lactis* and *Saccharomyces* species, e.g. *Saccharomyces cerevisiae*.

Host cells according to the invention include plant cells, and the invention therefore extends to transgenic organisms, such as plants and parts thereof, which contain one or more cells of the invention. The cells may heterologously express the polypeptide of the invention or may heterologously contain one or more of the polynucleotides of the invention. The transgenic (or genetically modified) plant may therefore have inserted (e.g. stably) into its genome a sequence encoding one or more of the polypeptides of the invention. The transformation of plant cells can be performed using known techniques, for example using a Ti or a Ri plasmid from *Agrobacterium tumefaciens*. The plasmid (or vector) may thus contain sequences necessary to infect a plant, and derivatives of the Ti and/or Ri plasmids may be employed.

Alternatively direct infection of a part of a plant, such as a leaf, root or stem can be effected. In this technique the plant to be infected can be wounded, for example by cutting the plant with a razor or puncturing the plant with a needle or rubbing the plant with an abrasive. The wound is then innoculated with the *Agrobacterium*. The plant or plant part can then be grown on a suitable culture medium and allowed to develop into a mature plant. Regeneration of transformed cells into genetically modified plants can be achieved by using known techniques, for example by selecting transformed shoots using an antibiotic and by sub-culturing the shoots on a medium containing the appropriate nutrients, plant hormones and the like.

The invention also includes cells that have been modified to express the cellobiohydrolase of the invention or a variant thereof. Such cells include transient, or preferably stable higher eukaryotic cell lines, such as mammalian cells or insect cells, lower eukaryotic cells, such as yeast and (e.g. filamentous) fungal cells or prokaryotic cells such as bacterial cells.

It is also possible for the proteins of the invention to be transiently expressed in a cell line or on a membrane, such as for example in a baculovirus expression system. Such systems, which are adapted to express the proteins according to the invention, are also included within the scope of the present invention.

According to the present invention, the production of the polypeptide of the invention can be effected by the culturing of microbial expression hosts, which have been transformed with one or more polynucleotides of the present invention, in a conventional nutrient fermentation medium.

The invention further relates to a method of producing a Mutant CBH comprising the steps of:
(a) culturing the host cell according to the invention in a suitable culture medium under suitable conditions to produce Mutant CBH;
(b) obtaining said produced Mutant CBH; and optionally
(c) purifying said Mutant CBH to provide a purified Mutant CBH product.

The invention further relates to an enzyme composition comprising one or more Mutant CBH according to the invention and or produced according to the method of the invention.

Further the invention related to a process for the degradation of ligno-cellulosic or hemi-cellulosic material, wherein ligno-cellulosic or hemi-cellulosic material is contacted with an enzyme composition according to invention. In an embodiment, in such a process of the invention, one or more sugar is produced. In an embodiment, the produced sugar is fermented to give a fermentation product. In an embodiment, the fermentation product is one or more of ethanol, butanol, lactic acid, a plastic, an organic acid, a solvent, an animal feed supplement, a pharmaceutical, a vitamin, an amino acid, an enzyme or a chemical feedstock.

Polypeptide/Enzyme Production

The recombinant host cells according to the invention may be cultured using procedures known in the art. For each combination of a promoter and a host cell, culture conditions are available which are conducive to the expression the DNA sequence encoding the polypeptide. After reaching the desired cell density or titre of the polypeptide the culture is stopped and the polypeptide is recovered using known procedures.

The fermentation medium can comprise a known culture medium containing a carbon source (e.g. glucose, maltose, molasses, starch, cellulose, xylan, pectin, lignocellolytic biomass hydrolysate, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). Optionally, an inducer (e.g. cellulose, pectin, xylan, maltose, maltodextrin or xylogalacturonan) may be included.

The selection of the appropriate medium may be based on the choice of expression host and/or based on the regulatory requirements of the expression construct. Such media are known to those skilled in the art. The medium may, if desired, contain additional components favouring the transformed expression hosts over other potentially contaminating microorganisms.

The fermentation can be performed over a period of from about 0.5 to about 30 days. It may be a batch, continuous or fed-batch process, suitably at a temperature in the range of, for example, from about 0 to about 45° C. and/or at a pH, for example, from about 2 to about 10. Preferred fermentation conditions are a temperature in the range of from about 20 to about 37° C. and/or at a pH of from about 3 to about 9. The appropriate conditions are usually selected based on the choice of the expression host and the protein to be expressed.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means.

Enzyme Compositions

The invention further provides enzyme composition comprising one or more mutant cellobiohydrolase. In one embodiment, the enzyme composition comprises one or more Mutant CBH, one or more cellulase and/or a hemicellulase and/or a pectinase.

An enzyme composition of the invention may comprise one, two three or more classes of cellulase, for example one, two or all of an endo-1,4-β-glucanase (EG) including preferably a GH61, an exo-cellobiohydrolase (CBH) and a β-glucosidase (BGL).

An enzyme composition of the invention may comprise a polypeptide which has the same enzymatic activity, for example the same type of cellulose, hemicellulase and/or pectinase activity as that provided by a polypeptide of the invention.

An enzyme composition of the invention may comprise a polypeptide which has a different type of cellulase activity and/or hemicellulase activity and/or pectinase activity than that provided by a polypeptide of the invention. For example, a composition of the invention may comprise one type of cellulase and/or hemicellulase activity and/or pectinase activity provided by a polypeptide of the invention and a second type of cellulase and/or hemicellulase activity and/or pectinase activity provided by an additional hemicellulase/pectinase.

Herein, a cellulase is any polypeptide which is capable of degrading or modifying cellulose. A polypeptide which is capable of degrading cellulose is one which is capable of catalysing the process of breaking down cellulose into smaller units, either partially, for example into cellodextrins, or completely into glucose monomers. A cellulase according to the invention may give rise to a mixed population of cellodextrins and glucose monomers when contacted with the cellulase. Such degradation will typically take place by way of a hydrolysis reaction.

Herein, a hemicellulase is any polypeptide which is capable of degrading or modifying hemicellulose. That is to say, a hemicellulase may be capable of degrading or modifying one or more of xylan, glucuronoxylan, arabinoxylan, glucomannan and xyloglucan. A polypeptide which is capable of degrading a hemicellulose is one which is capable of catalysing the process of breaking down the hemicellulose into smaller polysaccharides, either partially, for example into oligosaccharides, or completely into sugar monomers, for example hexose or pentose sugar monomers. A hemicellulase according to the invention may give rise to a mixed population of oligosaccharides and sugar monomers when contacted with the hemicellulase. Such degradation will typically take place by way of a hydrolysis reaction.

Herein, a pectinase is any polypeptide which is capable of degrading or modifying pectin. A polypeptide which is capable of degrading pectin is one which is capable of catalysing the process of breaking down pectin into smaller units, either partially, for example into oligosaccharides, or completely into sugar monomers. A pectinase according to the invention may give rise to a mixed population of oligosacchardies and sugar monomers when contacted with the pectinase. Such degradation will typically take place by way of a hydrolysis reaction.

Herein, an endo-β-1,4-glucanase (EC 3.2.1.4) is any polypeptide which s capable of catalysing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may also be referred to as cellulase, avicelase, β-1,4-endoglucan hydrolase, β-1,4-glucanase, carboxymethyl cellulase, celludextrinase, endo-1,4-β-D-glucanase, endo-1,4-β-D-glucanohydrolase, endo-1,4-β-glucanase or endoglucanase. GH61 endoglucanases (EC 3.2.1.4) were originally classified as a glycoside hydrolase family based on measurement of very weak endo-1,4-b-D-glucanase activity in one family member. The structure and mode of action of these enzymes are certainly non-canonical and they cannot be considered as bona fide glycosidases. However, they are kept in the CAZy classification on the basis of their capacity to enhance the breakdown of lignocellulose when used in conjunction with a cellulase or a mixture of cellulases.

Herein, a β-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

Herein a β-(1,3)(1,4)-glucanase (EC 3.2.1.73) is any polypeptide which is capable of catalyzing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucans when the glucose residue whose reducing group is involved in the linkage to be hydrolysed is itself substituted at C-3. Alternative names include endo-1,3-beta-glucanase, laminarinase, 1,3-(1,3;1,4)-beta-D-glucan 3 (4) glucanohydrolase; substrates include laminarin, lichenin and cereal beta-D-glucans.

Accordingly, a composition of the invention may comprise, in addition to Mutant CBH one or more of any cellulase, for example, a cellobiohydrolase (e.g. CBH-II), an endo-β-1,4-glucanase, a β-glucosidase or a β-(1,3)(1,4)-glucanase.

An enzyme composition according to the invention may comprise in addition one or more of the following enzyme activities:

endoxylanase (EC 3.2.1.8), β-xylosidase (EC 3.2.1.37), α-L-arabinofuranosidase (EC 3.2.1.55), α-D-glucuronidase (EC 3.2.1.139), xylan alpha-1,2-glucuronosidase (EC 3.2.1.131), feruloyl esterase (EC 3.1.1.73), coumaroyl esterase (EC 3.1.1.73), α-galactosidase (EC 3.2.1.22), β-galactosidase (EC 3.2.1.23), β-mannanase (EC 3.2.1.78), β-mannosidase (EC 3.2.1.25), endo-polygalacturonase (EC 3.2.1.15), pectin methyl esterase (EC 3.1.1.11), endo-galactanase (EC 3.2.1.89), endo-pectin lyase (EC 4.2.2.10), pectate lyase (EC 4.2.2.2), alpha rhamnosidase (EC 3.2.1.40), exo-galacturonase (EC 3.2.1.82), exo-galacturonase (EC 3.2.1.67), exopolygalacturonate lyase (EC 4.2.2.9), rhamnogalacturonan hydrolase, rhamnogalacturonan lyase, rhamnogalacturonan acetyl, rhamnogalacturonan galacturonohydrolase, xylogalacturonase, α-L-arabinofuranosidase (EC 3.2.1.55), endo-arabinanase (EC 3.2.1.99), protease (3.4), lipase, ligninase, e.g. lignin peroxidases (EC 1.11.1), manganese peroxidases (EC 1.11.1.13), laccases (EC 1.10.3.2) and feruloyl esterases (EC 3.1.1.73), hexosyltransferase" (2.4.1-). Glucuronidase, e.g. β-glucuronidase (EC 3.2.1.31), hyalurono-glucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139), an expansin or expansin-like protein, such as a swollenin (see Salheimo et al., Eur. J. Biohem. 269, 4202-4211, 2002) or a swollenin-like protein, scaffoldins and cellulose integrating proteins.

A composition of the invention may be composed of a member of each of the classes of the polypeptides mentioned above, several members of one polypeptide class, or any combination of these polypeptide classes.

A composition of the invention may be composed of polypeptides, for example enzymes, from (1) commercial suppliers; (2) cloned genes expressing polypeptides, for example enzymes; (3) complex broth (such as that resulting from growth of a microbial strain in media, wherein the strains secrete proteins and enzymes into the media; (4) cell lysates of strains grown as in (3); and/or (5) plant material expressing polypeptides, for example enzymes. Different polypeptides, for example enzymes in a composition of the invention may be obtained from different sources.

In an embodiment, CBHI is provided in an enzyme composition that comprises BG, EG and CBHII. In an embodiment thereof, the amounts of enzymes are chosen so that BG is present at 2-12%, CBHI at 10-65%, CBHII at 10-40% and EG at 12-70%, or in an embodiment thereof BG at 4-12%, EG at 18-50%, CBI-III at 10-35% and CBHI at 10-60% of the total protein dose (w/w).

Use of the Polypeptides

The polypeptides and enzyme compositions according to the invention may be used in many different applications. For instance they may be used to produce fermentable sugars. The fermentable sugars can then, as part of a biofuel process, be converted into biogas or ethanol, butanol, isobutanol, 2 butanol or other suitable substances. Alternatively the polypeptides and their compositions may be used as enzyme, for instance in production of food products, in detergent compositions, in the paper and pulp industry and in antibacterial formulations, in pharmaceutical products such as throat lozenges, toothpastes, and mouthwash. Some of the uses will be illustrated in more detail below.

In the uses and methods described below, the components of the compositions described above may be provided concomitantly (i.e. as a single composition per se) or separately or sequentially.

The invention also relates to the use of the cellobiohydrolase according to the invention and compositions comprising such an enzyme in industrial processes.

Despite the long term experience obtained with these processes, the cellobiohydrolase according to the invention may feature a number of significant advantages over enzymes currently used. Depending on the specific application, these advantages may include aspects such as lower production costs, higher specificity towards the substrate, reduced antigenicity, fewer undesirable side activities, higher yields when produced in a suitable microorganism, more suitable pH and temperature ranges, non-inhibition by hydrophobic, lignin-derived products or less product inhibition or, in the case of the food industry a better taste or texture of a final product as well as food grade and kosher aspects.

In principle, a cellobiohydrolase or composition of the invention may be used in any process which requires the treatment of a material which comprises polysaccharide. Thus, a polypeptide or composition of the invention may be used in the treatment of polysaccharide material. Herein, polysaccharide material is a material which comprises or consists essential of one or, more typically, more than one polysaccharide.

Typically, plants and material derived therefrom comprise significant quantities of non-starch polysaccharide material. Accordingly, a polypeptide of the invention may be used in the treatment of a plant or fungal material or a material derived therefrom.

Suitable Carbohydrate Materials

A non-starch carbohydrate suitable for modification by a Mutant CBH of the invention is lignocellulose. The major polysaccharides comprising different lignocellulosic residues, which may be considered as a potential renewable feedstock, are cellulose (glucans), hemicelluloses (xylans, heteroxylans and xyloglucans). In addition, some hemicellulose may be present as glucomannans, for example in wood-derived feedstocks. The enzymatic hydrolysis of these polysaccharides to soluble sugars, for example glucose, xylose, arabinose, galactose, fructose, mannose, rhamnose, ribose, D-galacturonic acid and other hexoses and pentoses occurs under the action of different enzymes acting in concert.

In addition, pectins and other pectic substances such as arabinans may make up considerably proportion of the dry mass of typically cell walls from non-woody plant tissues (about a quarter to half of dry mass may be pectins).

Accordingly, a composition of the invention may be tailored in view of the particular feedstock (also called substrate) which is to be used. That is to say, the spectrum of activities in a composition of the invention may vary depending on the feedstock in question.

Enzyme combinations or physical treatments can be administered concomitantly or sequentially. The enzymes can be produced either exogenously in microorganisms, yeasts, fungi, bacteria or plants, then isolated and added to the lignocellulosic feedstock. Alternatively, the enzymes are produced, but not isolated, and crude cell mass fermentation broth, or plant material (such as corn stover), and the like are added to the feedstock. Alternatively, the crude cell mass or enzyme production medium or plant material may be treated to prevent further microbial growth (for example, by heating or addition of antimicrobial agents), then added to the feedstock. These crude enzyme mixtures may include the organism producing the enzyme.

Alternatively, the enzyme may be produced in a fermentation that uses feedstock (such as corn stover) to provide nutrition to an organism that produces an enzyme(s). In this manner, plants that produce the enzymes may serve as the lignocellulosic feedstock and be added into lignocellulosic feedstock.

Lignocellulose

An important component of plant non-starch polysaccharide material is lignocellulose (also referred to herein as lignocellulolytic biomass). Lignocellulose is plant material that comprises cellulose and hemicellulose and lignin. The carbohydrate polymers (cellulose and hemicelluloses) are tightly bound to the lignin by hydrogen and covalent bonds. Accordingly, a polypeptide of the invention may be used in the treatment of lignocellulolytic material. Herein, lignocellulolytic material is a material which comprises or consists essential of lignocellulose. Thus, in a method of the invention for the treatment of a non-starch polysaccharide, the non-starch polysaccharide may be a lignocellulosic material/biomass.

Accordingly, the invention provides a method of treating a substrate comprising non-starch polysaccharide in which the treatment comprises the degradation and/or hydrolysis and/or modification of cellulose and/or hemicellulose and/or a pectic substance.

Degradation in this context indicates that the treatment results in the generation of hydrolysis products of cellulose and/or hemicellulose and/or a pectic substance, i.e. saccharides of shorter length are present as result of the treatment than are present in a similar untreated non-starch polysaccharide. Thus, degradation in this context may result in the liberation of oligosaccharides and/or sugar monomers.

All plants contain non-starch polysaccharide as do virtually all plant-derived polysaccharide materials. Accordingly, in a method of the invention for the treatment of substrate comprising a non-starch polysaccharide, said substrate may be provided in the form of a plant or a plant derived material or a material comprising a plant or plant derived material, for example a plant pulp, a plant extract, a foodstuff or ingredient therefore, a fabric, a textile or an item of clothing.

Lignocellulolytic biomass suitable for use in the invention includes biomass and can include virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane bagasse, corn, corn husks, corn cobs, corn kernel including fiber from kernels, products and by-products from milling of grains such as corn, wheat and barley (including wet milling and dry milling) often called "bran or fibre". The biomass can also be, but is not limited to, herbaceous material, agricultural biomass, forestry residues, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforestated singularly or in any combination or mixture thereof. Further examples of suitable biomass are orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, prairie grass, gamagrass, foxtail; sugar beet pulp, citrus fruit pulp, seed hulls, cellulosic animal wastes, lawn clippings, cotton, seaweed, trees, shrubs, grasses, wheat, wheat straw, sugar cane bagasse, corn, corn husks, corn kernel, fiber from kernels, products and by-products from wet or dry milling of grains, municipal solid waste, waste paper, yard waste, herbaceous material, agricultural residues, forestry residues, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, hard or soft wood, organic waste material generated from an agricultural process, forestry wood waste, or a combination of any two or more thereof.

Apart from virgin biomass or feedstocks already processed in food and feed or paper and pulping industries, the biomass/feedstock may additionally be pretreated with heat, mechanical and/or chemical modification or any combination of such methods in order to enhance enzymatic degradation.

Pretreatment

Before enzymatic treatment, the lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220 C for 1 to 30 minutes.

After the pretreatment step, a liquefaction/hydrolysis or presaccharification step involving incubation with an enzyme or enzyme mixture can be utilized. The presaccharification step can be performed at many different temperatures but it is preferred that the presaccharification occur at the temperature best suited to the enzyme mix being tested, or the predicted enzyme optimum of the enzymes to be tested. The temperature of the presaccharification may range from about 10° C. to about 95° C., about 20° C. to about 85° C., about 30° C. to about 70° C., about 40° C. to about 60° C., about 37° C. to about 50° C., preferably about 37° C. to about 80° C., more preferably about 60-70° C. even more preferably around 65° C. The pH of the presaccharification mixture may range from about 2.0 to about 10.0, but is preferably about 3.0 to about 7.0, more preferably about 4.0 to about 6.0, even more preferably about 4.0 to about 5.0. Again, the pH may be adjusted to maximize enzyme activity and may be adjusted with the addition of the enzyme. Comparison of the results of the assay results from this test will allow one to modify the method to best suit the enzymes being tested.

The liquefaction/hydrolysis or presaccharification step reaction may occur from several minutes to several hours, such as from about 1 hour to about 120 hours, preferably from about 2 hours to about 48 hours, more preferably from about 2 to about 24 hours, most preferably for from about 2 to about 6 hours. The cellulase treatment may occur from several minutes to several hours, such as from about 6 hours to about 120 hours, preferably about 12 hours to about 72 hours, more preferably about 24 to 48 hours.

Biomass may thus undergo various pretreatments in order to make cellulose more accessible to enzymatic breakdown (hydrolysis) and solubilize hemicellulose sugars. "Features of Promising Technologies for Pretreatment of Lignocellulosic Biomass," Bioresource Technology 96(3), 673-86. Yi Zheng, Zhongli Pan, Ruihong Zhang, Overview of biomass pre-treatment for cellulosic ethanol production. Int J Agric & Biol Eng, 2009; 2(3): 51-68

Saccharification

The invention provides a method for producing a sugar from a lignocellulosic material which method comprises contacting a polypeptide of the invention to a composition of the invention with the lignocellulosic material.

Such a method allows free sugars (monomers) and/or oligosaccharides to be generated from lignocellulosic biomass. These methods involve converting lignocellulosic biomass to free sugars and small oligosaccharides with a polypeptide or composition of the invention.

The process of converting a complex carbohydrate such as lignocellulose into sugars preferably allows conversion into fermentable sugars. Such a process may be referred to as "saccharification." Accordingly, a method of the invention may result in the liberation of one or more hexose and/or pentose sugars, such as one or more of glucose, xylose, arabinose, galactose, galacturonic acid, glucuronic acid, mannose, rhamnose, ribose and fructose.

Accordingly, another aspect of the invention includes methods that utilize the polypeptide of composition of the invention described above together with further enzymes or physical treatments such as temperature and pH to convert the lignocellulosic plant biomass to sugars and oligosaccharides.

While the composition has been discussed as a single mixture it is recognized that the enzymes may be added sequentially where the temperature, pH, and other conditions may be altered to increase the activity of each individual enzyme. Alternatively, an optimum pH and temperature can be determined for the enzyme mixture.

The enzymes are reacted with substrate under any appropriate conditions. For example, enzymes can be incubated at about 25° C., about 30° C., about 35° C., about 37° C., about 40° C., about 45° C., about 50° C., about 55° C., about 60° C., about 65° C., about 70° C., about 75° C., about 80° C., about 85° C., about 90° C. or higher. That is, they can be incubated at a temperature of from about 20° C. to about 95° C., for example in buffers of low to medium ionic strength and/or from low to neutral pH. By "medium ionic strength" is intended that the buffer has an ion concentration of about 200 millimolar (mM) or less for any single ion component. The pH may range from about pH 2.5, about pH 3.0, about pH 3.5, about pH 4.0, about pH 4.5, about pH 5, about pH 5.5, about pH 6, about pH 6.5, about pH 7, about pH 7.5, about pH 8.0, to about pH 8.5. Generally, the pH range will be from about pH 3.0 to about pH 7. For the production of ethanol an acidic medium is preferred, e.g. pH=4, whereas for the production of biogas neutral pH, e.g. pH=7 is desirable. Incubation of enzyme combinations under these conditions results in release or liberation of substantial amounts of the sugar from the lignocellulose. By substantial amount is intended at least 20%, 30%, 40%, 50%, 60%, 70%, 80%, 90%, 95% or more of available sugar.

The polypeptides, such as enzymes, can be produced either exogenously in microorganisms, yeasts, fungi, bacteria or plants, then isolated and added, for example, to lignocellulosic feedstock. Alternatively, the enzymes are produced, but not isolated, and crude cell mass fermentation broth, or plant material (such as corn stover), and the like may be added to, for example, the feedstock. Alternatively, the crude cell mass or enzyme production medium or plant material may be treated to prevent further microbial growth (for example, by heating or addition of antimicrobial agents), then added to, for example, a feedstock. These crude enzyme mixtures may include the organism producing the enzyme. Alternatively, the enzyme may be produced in a fermentation that uses feedstock (such as corn stover) to provide nutrition to an organism that produces an enzyme(s). In this manner, plants that produce the enzymes may themselves serve as a lignocellulosic feedstock and be added into lignocellulosic feedstock.

Fermentation of Sugars

The fermentable sugars can be converted to useful value-added fermentation products, non-limiting examples of which include amino acids, vitamins, pharmaceuticals, animal feed supplements, specialty chemicals, chemical feedstocks, plastics, solvents, fuels, or other organic polymers, lactic acid, and ethanol, including fuel ethanol. In particular the sugars may be used as feedstocks for fermentation into chemicals, plastics, such as for instance succinic acid and (bio) fuels, including ethanol, methanol, butanol synthetic liquid fuels and biogas.

For instance, in the method of the invention, an enzyme or combination of enzymes acts on a lignocellulosic substrate or plant biomass, serving as the feedstock, so as to convert this complex substrate to simple sugars and oligosaccharides for the production of ethanol or other useful fermentation products.

Sugars released from biomass can be converted to useful fermentation products such a one of those including, but not limited to, amino acids, vitamins, pharmaceuticals, animal feed supplements, specialty chemicals, chemical feedstocks, plastics, and ethanol, including fuel ethanol.

Accordingly, the invention provides a method for the preparation of a fermentation product, which method comprises:
 a. degrading lignocellulose using a method as described herein; and
 b. fermentation of the resulting material,
thereby to prepare a fermentation product.

The fermentation may be carried out under aerobic or anaerobic conditions. Preferably, the process is carried out under micro-aerophilic or oxygen limited conditions.

An anaerobic fermentation process is herein defined as a fermentation process run in the absence of oxygen or in which substantially no oxygen is consumed, preferably about 5 or less, about 2.5 or less or about 1 mmol/L/h or less, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6 and even more preferably at least about 7 mmol/L/h.

A method for the preparation of a fermentation product may optionally comprise recovery of the fermentation product.

SSF

Fermentation and Saccharification may also be executed in Simultaneous Saccharification and Fermentation (SSF) mode. One of the advantages of this mode is reduction of the sugar inhibition on enzymatic hydrolysis (Sugar inhibition on cellulases is described by Caminal B&B Vol XXVII Pp 1282-1290).

Fermentation Products

Fermentation products which may be produced according to the invention include amino acids, vitamins, pharmaceuticals, animal feed supplements, specialty chemicals, chemical feedstocks, plastics, solvents, fuels, or other organic polymers, lactic acid, and ethanol, including fuel ethanol (the term "ethanol" being understood to include ethyl alcohol or mixtures of ethyl alcohol and water).

Specific value-added products that may be produced by the methods of the invention include, but not limited to, biofuels (including ethanol and butanol and a biogas); lactic acid; a plastic; a specialty chemical; an organic acid, including citric acid, succinic acid, fumaric acid, itaconic acid and maleic acid; 3-hydroxy-propionic acid, acrylic acid; acetic acid; 1,3-propane-diol; ethylene, glycerol; a solvent; an animal feed supplement; a pharmaceutical, such as a β-lactam antibiotic or a cephalosporin; vitamins; an amino acid, such as lysine, methionine, tryptophan, threonine, and aspartic acid; an industrial enzyme, such as a protease, a cellulase, an amylase, a glucanase, a lactase, a lipase, a lyase, an oxidoreductases, a transferase or a xylanase; and a chemical feedstock.

Biogas

The invention also provides use of a polypeptide or composition a described herein in a method for the preparation of biogas. Biogas typically refers to a gas produced by the biological breakdown of organic matter, for example non-starch carbohydrate containing material, in the absence of oxygen. Biogas originates from biogenic material and is a type of biofuel. One type of biogas is produced by anaerobic digestion or fermentation of biodegradable materials such as biomass, manure or sewage, municipal waste, and energy crops. This type of biogas is comprised primarily of methane and carbon dioxide. The gas methane, can be combusted or oxidized with oxygen. Air contains 21% oxygen. This energy release allows biogas to be used as a fuel. Biogas can be used as a low-cost fuel in any country for any heating purpose, such as cooking. It can also be utilized in modern waste management facilities where it can be used to run any type of heat engine, to generate either mechanical or electrical power.

The first step in microbial biogas production consists in the enzymatic degradation of polymers and complex substrates (for example non-starch carbohydrate). Accordingly, the invention provides a method for preparation of a biogas in which a substrate comprising non-starch carbohydrate is contacted with a polypeptide or composition of the invention, thereby to yield fermentable material which may be converted into a biogas by an organism such as a microorganism. In such a method, a polypeptide of the invention may be provided by way of an organism, for example a microorganism which expresses such a polypeptide.

Use of Enzymes in Food Products

The polypeptides and compositions of the invention may be used in a method of processing plant material to degrade or modify the cellulose or hemicellulose or pectic substance constituents of the cell walls of the plant or fungal material. Such methods may be useful in the preparation of food product. Accordingly, the invention provides a method for preparing a food product which method comprises incorporating a polypeptide or composition of the invention during preparation of the food product.

The invention also provides a method of processing a plant material which method comprises contacting the plant material with a polypeptide or composition of the invention to degrade or modify the cellulose in the (plant) material. Preferably the plant material is a plant pulp or plant extract, such as juices.

The present invention also provides a method for reducing the viscosity, clarity and/or filterability of a plant extract which method comprises contacting the plant extract with a polypeptide or composition of the invention in an amount effective in degrading cellulose or hemicellulose or pectic substances contained in the plant extract.

Plant and cellulose/hemicellulose/pectic substance-containing materials include plant pulp, parts of plants and plant extracts. In the context of this invention an extract from a plant material is any substance which can be derived from plant material by extraction (mechanical and/or chemical), processing or by other separation techniques. The extract may be juice, nectar, base, or concentrates made thereof. The plant material may comprise or be derived from vegetables, e.g., carrots, celery, onions, legumes or leguminous plants (soy, soybean, peas) or fruit, e.g., pome or seed fruit (apples, pears, quince etc.), grapes, tomatoes, citrus (orange, lemon, lime, mandarin), melons, prunes, cherries, black currants, redcurrants, raspberries, strawberries, cranberries, pineapple and other tropical fruits, trees and parts thereof (e.g. pollen, from pine trees), or cereal (oats, barley, wheat, maize, rice). The material (to be hydrolysed) may also be agricultural residues, such as sugar beet pulp, corn cobs, wheat straw, (ground) nutshells, or recyclable materials, e.g. (waste) paper.

The polypeptides of the invention can thus be used to treat plant material including plant pulp and plant extracts. They may also be used to treat liquid or solid foodstuffs or edible foodstuff ingredients, or be used in the extraction of coffee, plant oils, starch or as a thickener in foods.

Typically, the polypeptides of the invention are used as a composition/enzyme preparation as described above. The composition will generally be added to plant pulp obtainable by, for example mechanical processing such as crushing or milling plant material. Incubation of the composition with the plant will typically be carried out for at time of from 10 minutes to 5 hours, such as 30 minutes to 2 hours, preferably for about 1 hour. The processing temperature is preferably from about 10° C. to about 55° C., e.g. from about 15° C. to about 25° C., optimally about 20° C. and one can use from about 10 g to about 300 g, preferably from about 30 g to about 70 g, optimally about 50 g of enzyme per ton of material to be treated.

All of the enzyme(s) or their compositions used may be added sequentially or at the same time to the plant pulp. Depending on the composition of the enzyme preparation the plant material may first be macerated (e.g. to a pure) or liquefied. Using the polypeptides of the invention processing parameters such as the yield of the extraction, viscosity of the extract and/or quality of the extract can be improved.

Alternatively, or in addition to the above, a polypeptide of the invention may be added to the raw juice obtained from pressing or liquefying the plant pulp. Treatment of the raw juice will be carried out in a similar manner to the plant pulp in respect of dosage, temperature and holding time. Again, other enzymes such as those discussed previously may be included. Typical incubation conditions are as described in the previous paragraph.

Once the raw juice has been incubated with the polypeptides of the invention, the juice is then centrifuged or (ultra) filtered to produce the final product.

After treatment with the polypeptide of the invention the (end) product can be heat treated, e.g. at about 100° C. for a time of from about 1 minute to about 1 hour, under conditions to partially or fully inactivate the polypeptide(s) of the invention.

A composition containing a polypeptide of the invention may also be used during the preparation of fruit or vegetable purees.

The polypeptide of the invention may also be used in brewing, wine making, distilling or baking. It may therefore used in the preparation of alcoholic beverages such as wine and beer. For example it may improve the filterability or clarity, for example of beers, wort (e.g. containing barley and/or sorghum malt) or wine.

Furthermore, a polypeptide or composition of the invention may be used for treatment of brewers spent grain, i.e. residuals from beer wort production containing barley or malted barley or other cereals, so as to improve the utilization of the residuals for, e.g., animal feed.

The protein may assist in the removal of dissolved organic substances from broth or culture media, for example where distillery waste from organic origin is bioconverted into microbial biomass. The polypeptide of the invention may improve filterability and/or reduce viscosity in glucose syrups, such as from cereals produced by liquefaction (e.g. with α-amylase).

In baking the polypeptide may improve the dough structure, modify its stickiness or suppleness, improve the loaf volume and/or crumb structure or impart better textural characteristics such as break, shread or crumb quality.

The preparation of a dough is well known in the art and comprises mixing of said ingredients and processing aids and one or more moulding and optionally fermentation steps. The preparation of frozen dough is described by Kulp and Lorenz in Frozen and Refrigerated Doughs and Batters.

Non-starch polysaccharides (NSP) can increase the viscosity of the digesta which can, in turn, decrease nutrient availability and animal performance. The use of the mutant cellobiohydrolase of the present invention can improve phosphorus utilization as well as cation minerals and protein during animal digesta.

Adding specific nutrients to feed improves animal digestion and thereby reduces feed costs. A lot of feed additives are being currently used and new concepts are continuously developed. Use of specific enzymes like non-starch carbohydrate degrading enzymes could breakdown the fibre releasing energy as well as increasing the protein digestibility due to better accessibility of the protein when the fibre gets broken down. In this way the feed cost could come down as well as the protein levels in the feed also could be reduced.

Non-starch polysaccharides (NSPs) are also present in virtually all feed ingredients of plant origin. NSPs are poorly utilized and can, when solubilized, exert adverse effects on digestion. Exogenous enzymes can contribute to a better utilization of these NSPs and as a consequence reduce any anti-nutritional effects. Non-starch carbohydrate degrading enzymes of the present invention can be used for this purpose in cereal-based diets for poultry and, to a lesser extent, for pigs and other species.

A non-starch carbohydrate degrading polypeptide/enzyme of the invention (of a composition comprising the polypeptide/enzyme of the invention) may be used in the detergent industry, for example for removal from laundry of carbohydrate-based stains. A detergent composition may comprise a polypeptide/enzyme of the invention and, in addition, one or more of a cellulose, a hemicellulase, a pectinase, a protease, a lipase, a cutinase, an amylase or a carbohydrase.

Use of Enzymes in Detergent Compositions

A detergent composition comprising an a polypeptide or composition of the invention may be in any convenient form, for example a paste, a gel, a powder or a liquid. A liquid detergent may be aqueous, typically containing up to about 70% water and from about 0 to about 30% organic solvent or non-aqueous material.

Such a detergent composition may, for example, be formulated as a hand or machine laundry detergent composition including a laundry additive composition suitable for pretreatment of stained fabrics and a rinse added fabric softener composition, or be formulated as a detergent composition for use in general household hard surface cleaning operations, or be formulated for hand or machine dish washing operations. In general, the properties of the enzyme should be compatible with the aselected detergent (for example, pH-optimum, compatibility with other enzymatic and/or non-enzymatic ingredients, etc.) and the enzyme(s) should be present in an effective amount. A detergent composition may comprise a surfactant, for example an anionic or non-ionic surfactant, a detergent builder or complexing agent, one or more polymers, a bleaching system (for example an $H_2O_2$ source) or an enzyme stabilizer. A detergent composition may also comprise any other conventional detergent ingredient such as, for example, a conditioner including a clay, a foam booster, a sud suppressor, an anti-corrosion agent, a soil-suspending agent, an an-soil redeposition agent, a dye, a bactericide, an optical brightener, a hydrotropes, a tarnish inhibitor or a perfume.

Use of Enzymes in Paper and Pulp Processing

A polypeptide or composition of the present invention may be used in the paper and pulp industry, inter alia in the bleaching process to enhance the brightness of bleached pulps whereby the amount of chlorine used in the bleaching stages may be reduced, and to increase the freeness of pulps in the recycled paper process (Eriksson, K. E. L., Wood Science and Technology 24 (1990):79-101; Paice, et al., Biotechnol. and Bioeng. 32 (1988):235-239 and Pommier et al., Tappi Journal (1989):187-191). Furthermore, a polypeptide or composition of the invention may be used for treatment of lignocellulosic pulp so as to improve the bleachability thereof. Thereby the amount of chlorine need to obtain a satisfactory bleaching of the pulp may be reduced.

A polypeptide or composition of the invention may be used in a method of reducing the rate at which cellulose-containing fabrics become harsh or of reducing the harshness of cellulose-containing fabrics, the method comprising treating cellulose-containing fabrics with a polypeptide or composition as described above. The present invention further relates to a method providing colour clarification of coloured cellulose-containing fabrics, the method comprising treating coloured cellulose-containing fabrics with a polypeptide or composition as described above, and a method of providing a localized variation in colour of coloured cellulose-containing fabrics, the method comprising treating coloured cellulose-containing fabrics with a polypeptide or composition as described above. The methods of the invention may be carried out by treating cellulose-containing fabrics during washing. However, if desired, treatment of the fabrics may also be carried out during soaking or rinsing or simply by adding the polypeptide or composition as described above to water in which the fabrics are or will be immersed.

Other Enzyme Uses

In addition, a polypeptide or composition of the present invention can also be used in antibacterial formulation as well as in pharmaceutical products such as throat lozenges, toothpastes, and mouthwash.

The following Examples illustrate the invention:

Materials and Methods

DNA Procedures

Standard DNA procedures were carried out as described elsewhere (Sambrook et al., 1989, *Molecular cloning: a laboratory manual,* 2$^{nd}$ Ed., Cold Spring Harbor Laboratory Press, Cold Spring Harbor, N.Y.) unless otherwise stated. DNA was amplified using the proofreading enzyme Physion polymerase (Finnzymes). Restriction enzymes were from Invitrogen or New England Biolabs.

Mutants were designed having mutations at positions 6, 7, 34, 36, 41, 47, 48, 52, 77, 99, 101, 144, 171, 177, 192, 194, 195, 196, 198, 200, 205, 232, 243, 244, 245, 246, 247, 249, 255, 337, 343, 344, 346, 350, 367, 372, 375, 376, 393, and 396 of CBH-I. The corresponding codon optimized genes that express the Mutant CBH's were synthetically produced.

Using standard DNA procedures, for each positions as indicated hereinbefore, the codon was randomized and about 96 clones were tested covering about 15-17 different amino acids. The genes corresponding to the CBH mutants are transformed to *A. niger*. In order to obtain expression of the mutants as uniform as possible both the vector and the transformation protocols are optimised in order to target integration to preferred loci, which minimizes the chance of random integration as well as the introduction of multiple genes.

Method for CBHI Protein Determination

CBHI was quantified with LC-MS, using an experimental procedure adapted from the Absolute Quantification (AQUA) method (Gerber, M. W. et al. 2003, Absolute quantification of proteins and phosphoproteins from cell lysates by tandem MS, PNAS 100, p 6940-6945). The synthetic internal standard LYLLQDDETYQI*FK.LLNR containing stable heavy isotopes was used for quantification and method development. The standard was scaled by NMR quantification prior to the experiments to ensure that the correct absolute amount internal standard was added. Method optimization was performed using the supernatant of the strain expressing the WT CBHI with spiked internal standard. The digestion protocol was optimized based on the Trypsin cleavage site included in the internal standard, monitoring the un-cleaved and cleaved version of the internal standard.

CBHI mutant samples were processed in fresh lo-bind MTPs. TCA precipitation was performed for protein purification. BSA was added for improved protein precipitation. Precipitated protein was collected by centrifugation and the supernatant was removed. The protein pellets were solubilized in 8M urea containing the internal standard. Samples were diluted to <2M urea with $NH_4HCO_3$ and Trypsin was added for proteolytic digestion.

Samples were analyzes using an Accela-LTQ-Orbitrap. Quantification was performed by determining the ratio of the LC-MS area of the peptide from CBHI or CBHI mutants and the LC-MS area of the internal standard.

Method for CBHI Activity Determination

All CBH mutants are screened for activity on washed acid pretreated wheat straw, at 2% dm in acetate buffer at pH 4.5, in combination with a fixed amount of beta-glucosidase. The beta-glucosidase which was used in the mixture originates from *Talaromyces emersonii*, and was expressed in *Aspergillus niger*. Concentrated filtrates of the enzymes were produced as described in WO2004/030468. After growing *Aspergillus niger* containing the proper expression plasmids cell free supernatants were prepared by centrifugation of the fermentation broth at 5000×g for 30 minutes at 4° C. Optional the supernatant can be adjusted to pH=5 with 4 N KOH and sterile filtrated over a 2 μm (bottle-top) filter with suction to remove any fungal material. In addition the supernatants can be filtered further over a GF/A Whatmann Glass microfiber filter (150 mm Ø) to remove any solids. The supernatants may be concentrated and stored until use at 4° C. or frozen at −20° C.

The amount of BG and CBHI in this screening assay is 2-3 mg beta-glucosidase per g wheat straw dry matter, and 1-2 mg CBHI per g wheat straw dry matter. The incubations were carried out at at 65° C. for time periods ranging from 4 to 96 hours.

An alternative method would be to test the CBHI in a mix with BG, EG and CBHII, in which the ranges of the different enzymes can be chosen as follows BG at 4-12%, EG at 18-50%, CBHII at 10-35% and CBHI at 10-60% of the total protein dose of 10 mg per gram wheat straw dry matter. Incubations were done for time periods ranging from 4 to 96 hours, and were compared to a blank at start of the incubation. The reactions were terminated at the given time, by spinning down the residue, pipetting of the supernatant and freezing the samples until analysis. The method of screening for improved variants is not limited to the assays given above. Substrate may come from different origin. The way the pretreatment is carried out may differ. The conditions of the assays may be varied, e.g. saccharification at different pH or at different temperature. In addition the nature of the BG, EG, and CBHII might be changed as well as the assay may comprise one, two or three classes of cellulose, for example one, two or all of an endo-1,4-β-glucanase (EG), an exo-cellobio-hydrolase (CBH) and a β-glucosidase (BGL). In addition further accessory enzymes such as for example hemicellulases and/or pectinase may be added. The assay is set up in such a way that the target enzyme for improvement is the limiting factor with respect to performance.

Analysis was performed using flow-NMR. The $^1$H NMR spectra were recorded on a Bruker AVANCE II BEST NMR system operating at proton frequency 500 MHz and probe temperature 27° C.

The mutants showing the highest glucose and/or cellobiose release, were selected for further characterization.

An alternative method to screen the mutants was to incubate the supernatants with an artificial substrate, such as para-nitrophenol-beta-cellobioside, as described in "Kinetic parameters and mode of action of the cellobiohydrolases produced by *Talaromyces emersonii*, Biochimica et Biophysica Acta 1596 (2002):366-380.

Example 1

Activity of CBHI Mutants on pNP-Cellobioside

The amount of CBHI protein in the filtrated supernatant of shakeflask fermentations of transformants expressing CBHI (EBA205 and mutants) was determined using LC-MS. The samples were incubated containing 0.02 mg/mL CBHI protein, 3 mM pNP-cellobioside and 10 mM gluconolacton at 65° C., pH4.5 for 10 and 30 minutes.

From the table it is clear that the activity of the CBHI mutants has been improved both at 10 and 30 minutes measuring time.

TABLE 1

CBHI activity of mutants on pNP-cellobioside (U/mg). 1 U is the amount of enzyme able to release 1 μmol pNP per min/mL at assay conditions.

|  | CBHI activity (U/mg) 10 min | | CBHI activity (U/mg) 30 min | |
| --- | --- | --- | --- | --- |
| EBA205 | 0.47 | 100 | 0.45 | 100 |
| N247F | 0.58 | 123 | 0.52 | 116 |
| D77M | 0.60 | 128 | 0.52 | 116 |
| N247H | 0.82 | 174 | 0.68 | 151 |
| G357R | 0.58 | 123 | 0.52 | 111 |
| Q232A | 0.57 | 121 | 0.51 | 113 |
| S36E | 0.70 | 149 | 0.61 | 136 |
| K163N | 0.58 | 123 | 0.51 | 113 |
| F427I | 0.61 | 130 | 0.57 | 127 |

Example 2

Activity of CBHI Mutants on Pre-Treated Wheat Straw

The amount of CBHI protein in the filtrated supernatant of shakeflask fermentations of transformants expressing CBHI (EBA205 and mutants) was determined using LC-MS. The samples were incubated containing 1.0 mg/mL CBHI protein at 65° C., pH4.5 for 17 and 70 hours.

Results from table 2 clearly show improvement of CBHI mutants in releasing glucose from pre-treated wheat straw.

TABLE 2

CBHI activity of mutants on pre-treated wheat straw. Activity is
given in mM glucose released at time points 17 and 70 hours.

|  | mM glucose released | | | |
|---|---|---|---|---|
|  | 17 hrs | | 70 hrs | |
| EBA205 | 3.7 | 100 | 7.4 | 100 |
| N247F | 4.4 | 118 | 6.5 | 89 |
| D77M | 4.6 | 123 | 6.7 | 91 |
| N247H | 5.7 | 152 | 8.4 | 115 |
| G357R | 4.3 | 115 | 6.3 | 86 |
| Q232A | 5.7 | 151 | 8.2 | 111 |
| S36E | 4.1 | 111 | 6.9 | 94 |
| K163N | 4.7 | 126 | 6.4 | 86 |
| F427I | 4.7 | 124 | 6.5 | 89 |

TABLE 3

CBHI mutant dose to obtain glucose releases similar to EBA205
at 1.5 mg/g DM at different time points.

|  | 5 hrs<br>12 mM Glc | 22 hrs<br>27 mM Glc | 46 hrs<br>37 mM Glc | 70 hrs<br>42 mM Glc |
|---|---|---|---|---|
| EBA205 | 1.5 | 1.5 | 1.5 | 1.5 |
| N247F | 0.9 | 1.2 | 1.3 | 1.1 |
| D77M | 0.8 | 1.1 | 1.3 | 2.0 |
| N247H | 0.6 | 0.9 | 1.0 | n.d. |
| G357R | 0.8 | 1.0 | 1.2 | 1.4 |
| Q232A | 1.0 | 1.3 | 1.2 | 1.2 |
| S36E | 0.8 | 1.0 | 1.0 | n.d. |
| K163N | 0.7 | 1.6 | n.d. | n.d. |
| F427I | 0.7 | 1.4 | 1.4 | n.d. |

(n.d. not determined)

Example 3

Dose Response Relations of CBHI Mutants in Cellulase Mix

The activity of the CBHI mutants in the cellulase mix has been tested at different dosages. The dosage of the mutant able to release the same amount of glucose as a 1.5 and 3.0 mg/mL dosage of EBA205 is determined and presented in Table 3 and 4, respectively.

The activity of the CBHI mutants was tested with an enzyme mix containing EG, BG and CBI-III in the ratio 4.1:1:2.8. The enzyme mix was dosed at 7.0 mg/gDM and different dosages of CBHI were added.

The dosage of the mutants able to release the same amount of glucose as a 1.5 and 3.0 mg/mL dosage of EBA205 is determined and presented in table 3 and 4.

Tables 3 and 4 clearly show that the CBHI mutants allow for a lower dosage of CBHI in the cellulase mix.

TABLE 4

CBHI mutant dose to obtain glucose releases similar to EBA205
at 3.0 mg/g DM at different time points.

|  | 5 hrs<br>15 mM Glc | 22 hrs<br>29 mM Glc | 46 hrs<br>39 mM Glc | 70 hrs<br>45 mM Glc |
|---|---|---|---|---|
| EBA205 | 3.0 | 3.0 | 3.0 | 3.0 |
| N247F | n.d. | 1.5 | 1.8 | 1.8 |
| D77M | 2.3 | 1.4 | 1.9 | 2.3 |
| N247H | 1.4 | 1.2 | 1.6 | n.d. |
| G357R | 1.7 | 1.3 | 1.6 | n.d. |
| Q232A | 2.1 | 2.3 | 1.4 | 2.3 |
| S36E | 1.7 | 1.5 | n.d. | n.d. |
| K163N | 1.9 | 2.0 | 2.2 | n.d. |
| F427I | 1.6 | 2.0 | n.d. | n.d. |

(n.d. not determined)

The invention claimed is:

1. A mutant cellobiohydrolase, being a mutant of SEQ ID NO;1, comprising a substitution at position N247(I,F,H,W) of SEQ ID NO: 1, wherein said mutant cellobiohydrolase comprises at least 50% sequence identity with SEQ ID NO: 1, and wherein said mutant cellobiohydrolase has cellobiohydrolase-I (CBHI) activity.

2. The mutant cellobiohydrolase according to claim 1, wherein said mutant comprises substitution N247F.

3. The mutant cellobiohydrolase according to claim 1, wherein said mutant comprises substitution N247H.

4. The mutant cellobiohydrolase according to claim 1, wherein CBH-I comprises the amino acid sequence as set out in SEQ ID NO: 1 and said mutant has a substitution or deletion at a position corresponding to at least one of residues F427, K163, G357, S36, D77, and/or Q232.

5. The mutant cellobiohydrolase according to claim 4, wherein said mutant comprises at least one of the following substitutions: F427I, K163N, G357R, S36E, D77M and/or Q232A.

6. The mutant cellobiohydrolase according to claim 1, wherein CBH-I comprises the amino acid sequence as set out in SEQ ID NO: 1 and said mutant comprises a substitution or deletion at a position corresponding to at least one of residues T52, V101, S192, T198, T246, T344, D346, A375 and/or A376.

7. The mutant cellobiohydrolase according to claim 6, wherein said mutant comprises at least one of the following substitutions: T52(G,M,Y,D,H,K,R), V101(T,I,F,H), S192 (A,I,F,Q,H), T198(A,C,V,P,D,H), T246(G,A,Y,N,H), T344 (A,S,C,L,I,Y,W), D346(P,F,G,R), A375(G,I, W,Y,H,K,R) and/or A376(T,V,L,Y,W,D).

8. The mutant cellobiohydrolase according to claim 7, wherein said mutant comprises at least one of the following substitutions: T52(M,D,R), V101(I,F), S192F, T198(A,H), T246N, T344(Y,C,L), D346(R,G), A375(Y,H) and/or A376 (Y,W).

9. The mutant cellobiohydrolase according to claim 8, wherein said mutant comprises at least one of the following substitutions: T52D, V101F, S192F, T198H, T246N, T344Y, D346G, A375Y and/or A376Y.

10. The mutant cellobiohydrolase claim 1, wherein said mutant comprises at least one deletion at a position corresponding to at least one of residues A6, T7, L34, V41,Y47, T48, S99, V144, S171, L177, N194, N195, A196, I200, S205, T243, Y244, S245, Y249, P255, Q337, D343, H350, V367, D372, T393, and/or V396.

11. A polynucleotide encoding the mutant cellobiohydrolase according to claim 1.

12. A nucleic acid construct comprising the polynucleotide of claim 11.

13. A host cell transformed with the nucleic acid construct of claim 12.

14. A method of producing a mutant cellobiohydrolase comprising:
   (a) culturing said host cell according to claim 13 in a suitable culture medium under suitable conditions to produce mutant cellobiohydrolase;
   (b) obtaining said produced mutant cellobiohydrolase; and optionally
   (c) purifying said mutant cellobiohydrolase to provide a purified mutant cellobiohydrolase.

15. An enzyme composition comprising at least one mutant cellobiohydrolase according to claim 1.

16. A process for degrading ligno-cellulosic or hemi-cellulosic material, said process comprising contacting said ligno-cellulosic or hemi-cellulosic material with an enzyme composition according to claim 15.

17. The process according to claim 16, wherein at least one sugar is produced.

18. The process according to produce a fermentation product comprising: (a) contacting ligno-cellulosic or hemi-cellulosic material with an enzyme composition according to claim 15 to produce at least one sugar, and (b) fermenting the produced sugar to give a fermentation product.

19. The process according to claim 18, wherein said fermentation product is at least one of a plastic, an organic acid, a solvent, a pharmaceutical, a vitamin, an amino acid, or an enzyme.

20. The process according to claim 19, wherein said solvent is ethanol or butanol.

21. The process according to claim 19, wherein said organic acid is lactic acid.

22. The process according to claim 18, wherein said fermentation product is an animal feed supplement.

* * * * *

```
SEQUENCE LISTING

<160> NUMBER OF SEQ ID NOS: 3

<210> SEQ ID NO 1
<211> LENGTH: 437
<212> TYPE: PRT
<213> ORGANISM: Talaromyces emersonii

<400> SEQUENCE: 1

Gln Gln Ala Gly Thr Ala Thr Ala Glu Asn His Pro Pro Leu Thr Trp
1               5                   10                  15

Gln Glu Cys Thr Ala Pro Gly Ser Cys Thr Thr Gln Asn Gly Ala Val
                20                  25                  30

Val Leu Asp Ser Asn Trp Arg Trp Val His Asn Val Gly Gly Tyr Thr
            35                  40                  45

Asn Cys Tyr Thr Gly Asn Thr Trp Asn Pro Thr Tyr Cys Pro Asp Asp
    50                  55                  60

Val Thr Cys Ala Glu Asn Cys Ala Leu Asp Gly Ala Asp Tyr Glu Gly
65                  70                  75                  80

Thr Tyr Gly Val Thr Ser Ser Gly Ser Glu Leu Arg Leu Asn Phe Val
                85                  90                  95

Thr Gly Ser Asn Val Gly Ser Arg Leu Tyr Leu Leu Gln Asp Asp Glu
            100                 105                 110

Thr Tyr Gln Ile Phe Lys Leu Leu Asn Arg Glu Phe Thr Phe Asp Val
        115                 120                 125
```

```
Asp Val Ser Asn Leu Pro Cys Gly Leu Asn Gly Ala Leu Tyr Phe Val
    130                 135                 140

Ala Met Asp Ala Asp Gly Val Ser Lys Tyr Pro Asn Asn Lys Ala
145                 150                 155                 160

Gly Ala Lys Tyr Gly Thr Gly Tyr Cys Asp Ser Gln Cys Pro Arg Asp
                165                 170                 175

Leu Lys Phe Ile Asp Gly Glu Gly Asn Val Glu Gly Trp Gln Pro Ser
            180                 185                 190

Ser Asn Asn Ala Asn Thr Gly Ile Gly Asp His Gly Ser Cys Cys Ala
        195                 200                 205

Glu Met Asp Val Trp Glu Ala Asn Ser Ile Ser Asn Ala Val Thr Pro
    210                 215                 220

His Pro Cys Asp Thr Pro Gly Gln Thr Met Cys Asp Gly Asp Asp Cys
225                 230                 235                 240

Gly Gly Thr Tyr Ser Thr Asn Arg Tyr Ala Gly Glu Cys Asp Pro Asp
                245                 250                 255

Gly Cys Asp Phe Asn Pro Tyr Arg Met Gly Asn Thr Ser Phe Tyr Gly
            260                 265                 270

Pro Gly Lys Ile Ile Asp Thr Thr Gln Pro Phe Thr Val Val Thr Gln
        275                 280                 285

Phe Leu Thr Asp Asp Gly Thr Asp Thr Gly Thr Leu Ser Glu Ile Lys
    290                 295                 300

Arg Phe Tyr Ile Gln Asn Gly Lys Val Ile Pro Gln Pro Asn Ser Asp
305                 310                 315                 320

Ile Ser Gly Val Thr Gly Asn Ser Ile Thr Thr Glu Phe Cys Thr Ala
                325                 330                 335

Gln Lys Gln Ala Phe Gly Asp Thr Asp Asp Phe Ser Gln His Gly Gly
            340                 345                 350

Leu Ala Lys Met Gly Ala Ala Met Gln Gln Gly Met Val Leu Val Met
        355                 360                 365

Ser Leu Trp Asp Asp Tyr Ala Ala Gln Met Leu Trp Leu Asp Ser Asp
    370                 375                 380

Tyr Pro Thr Asn Ala Ser Ala Thr Thr Pro Gly Val Ala Arg Gly Thr
385                 390                 395                 400

Cys Pro Thr Asp Ser Gly Val Pro Ser Gln Val Glu Ser Gln Ser Pro
                405                 410                 415

Asn Ser Tyr Val Thr Tyr Ser Asn Ile Lys Phe Gly Pro Ile Asn Ser
            420                 425                 430

Thr Phe Thr Ala Ser
        435

<210> SEQ ID NO 2
<211> LENGTH: 18
<212> TYPE: PRT
<213> ORGANISM: Talaromyces emersonii

<400> SEQUENCE: 2

Met Leu Arg Arg Ala Leu Leu Ser Ser Ala Ile Leu Ala Val
1               5                   10                  15

Lys Ala

<210> SEQ ID NO 3
<211> LENGTH: 1368
<212> TYPE: DNA
<213> ORGANISM: Artificial sequence
```

<220> FEATURE:
<223> OTHER INFORMATION: cDNA sequence of CBH-I (EBA205)

<400> SEQUENCE: 3

```
atgctccgcc gtgctcttct gctgagcagc tctgccatcc tggccgtcaa ggcccagcag      60
gctggtactg ccactgctga gaaccaccct cccttgacct ggcaggagtg cactgctcct     120
ggttcctgca ccactcagaa cggtgctgtt gtccttgaca gcaactggag atgggttcac     180
aacgtcggtg gttacaccaa ctgctacact ggcaacacct ggaaccccac ctactgcccc     240
gatgatgtca cctgcgctga gaactgcgct cttgacggtg ccgactacga gggtacctac     300
ggtgtcactt cttctggctc tgagctccgt ctgaacttcg tcaccggcag caacgtcggc     360
tctcgtctct acctcctcca ggatgacgag acctaccaga tcttcaagct cctcaaccgt     420
gagttcacct tcgatgttga tgtctccaac cttccttgcg gtctgaacgg tgctctgtac     480
ttcgtcgcca tggatgccga cggtggtgtc tccaagtacc caacaacaa ggccggtgcc     540
aagtacggta ctggctactg cgacagccag tgccccgtg acctcaagtt cattgacggc     600
gagggcaacg tcgagggctg gcagccctcc tccaacaacg ccaacactgg tatcggtgac     660
cacggctctt gctgcgctga gatggatgtc tgggaggcca actccatctc caacgccgtc     720
accccccacc cttgcgacac ccccggccag accatgtgcg atggtgatga ctgcggtggt     780
acctactcca ccaaccgcta cgccggtgag tgcgaccccg atggctgcga cttcaacccc     840
taccgcatgg gcaacacctc cttctacggc cctggcaaga tcattgacac cacccagccc     900
ttcaccgttg tcacccagtt cctgaccgat gacggcaccg acactggtac cctctccgag     960
atcaagcgct tctacatcca gaacggcaag gtcatccccc agcccaactc cgacatctcc    1020
ggtgtcaccg gcaactccat caccactgag ttctgcactg ctcagaagca ggctttcggt    1080
gacaccgatg acttctccca gcacggtggt cttgccaaga tgggtgctgc catgcagcag    1140
ggtatggtcc tggtcatgtc cctctgggat gactacgctg tcagatgct ctggctcgac    1200
tccgactacc ccaccaacgc ctccgccacc actcctggtg ttgctcgtgg tacctgcccc    1260
accgactctg tgttcctag ccaggttgag agccagtccc ccaactccta cgtgacctac    1320
tccaacatca agttcggtcc catcaactcc accttcactg catcgtaa               1368
```